(12) United States Patent
Sardi

(10) Patent No.: US 9,226,937 B2
(45) Date of Patent: Jan. 5, 2016

(54) COMPOSITIONS CONTAINING RESVERATROL AND NUCLEOTIDES

(71) Applicant: Resveratrol Partners, LLC, La Verne, CA (US)

(72) Inventor: William F. Sardi, La Verne, CA (US)

(73) Assignee: RESVERATROL PARTNERS, LLC, Las Vegas, NV (US)

( * ) Notice: Subject to any disclaimer, the term of this patent is extended or adjusted under 35 U.S.C. 154(b) by 0 days.

(21) Appl. No.: 14/551,565

(22) Filed: Nov. 24, 2014

(65) Prior Publication Data

US 2015/0080459 A1 Mar. 19, 2015

Related U.S. Application Data

(62) Division of application No. 13/679,299, filed on Nov. 16, 2012, now Pat. No. 8,916,528.

(60) Provisional application No. 61/560,482, filed on Nov. 16, 2011.

(51) Int. Cl.

| | | |
|---|---|---|
| *A01N 43/04* | (2006.01) | |
| *A61K 31/70* | (2006.01) | |
| *A61K 31/713* | (2006.01) | |
| *A61K 31/05* | (2006.01) | |
| *A61K 31/7064* | (2006.01) | |
| *A61K 31/6615* | (2006.01) | |
| *A61K 31/7068* | (2006.01) | |
| *A61K 31/7052* | (2006.01) | |
| *A61K 31/185* | (2006.01) | |
| *A61K 31/352* | (2006.01) | |
| *A61K 31/353* | (2006.01) | |
| *A61K 45/06* | (2006.01) | |

(52) U.S. Cl.
CPC ............... *A61K 31/713* (2013.01); *A61K 31/05* (2013.01); *A61K 31/185* (2013.01); *A61K 31/352* (2013.01); *A61K 31/353* (2013.01); *A61K 31/6615* (2013.01); *A61K 31/7052* (2013.01); *A61K 31/7064* (2013.01); *A61K 31/7068* (2013.01); *A61K 45/06* (2013.01)

(58) Field of Classification Search
None
See application file for complete search history.

(56) References Cited

U.S. PATENT DOCUMENTS

| | | |
|---|---|---|
| 4,952,396 A | 8/1990 | Sabin et al. |
| 5,211,956 A | 5/1993 | Sawai et al. |
| 5,258,189 A | 11/1993 | Efstathiou |
| 6,060,500 A | 5/2000 | Bonewald et al. |
| 6,086,910 A | 7/2000 | Howard et al. |
| 6,190,716 B1 | 2/2001 | Galbreath, Jr. |
| 6,368,617 B1 | 4/2002 | Hastings et al. |
| 6,469,055 B2 | 10/2002 | Lee et al. |
| 6,492,429 B1 | 12/2002 | Graus et al. |
| 6,572,882 B1 | 6/2003 | Vercauteren et al. |
| 6,605,296 B1 | 8/2003 | Stuckler |
| 6,642,277 B1 | 11/2003 | Howard et al. |
| 7,345,178 B2 | 3/2008 | Nunes et al. |
| 7,544,497 B2 | 6/2009 | Sinclair et al. |
| 2001/0039296 A1 | 11/2001 | Bagchi et al. |
| 2002/0110604 A1 | 8/2002 | Babish et al. |
| 2002/0146424 A1 | 10/2002 | Benza et al. |
| 2002/0176902 A1 | 11/2002 | Theoharides |
| 2003/0045544 A1 | 3/2003 | Schulz et al. |
| 2004/0014721 A1 | 1/2004 | Hensley et al. |
| 2004/0115309 A1 | 6/2004 | Harris |
| 2004/0116386 A1 | 6/2004 | Pifferi et al. |
| 2005/0096256 A1 | 5/2005 | Sinclair |
| 2005/0136537 A1 | 6/2005 | Sinclair |
| 2005/0158376 A1 | 7/2005 | Sardi et al. |
| 2005/0171027 A1 | 8/2005 | Sinclair et al. |
| 2005/0196469 A1 | 9/2005 | Thys-Jacobs |
| 2006/0025337 A1 | 2/2006 | Sinclair et al. |
| 2006/0084085 A1 | 4/2006 | Sinclair et al. |
| 2006/0111435 A1 | 5/2006 | Sinclair et al. |
| 2006/0159745 A1 | 7/2006 | Baksh |
| 2006/0229265 A1 | 10/2006 | Milburn et al. |
| 2006/0276393 A1 | 12/2006 | Milburn et al. |
| 2006/0276416 A1 | 12/2006 | Sinclair et al. |
| 2007/0014833 A1 | 1/2007 | Milburn et al. |
| 2007/0037809 A1 | 2/2007 | Nunes et al. |
| 2007/0037827 A1 | 2/2007 | Nunes et al. |
| 2007/0037865 A1 | 2/2007 | Nunes et al. |
| 2007/0043050 A1 | 2/2007 | Nunes et al. |

(Continued)

FOREIGN PATENT DOCUMENTS

| | | |
|---|---|---|
| JP | 1157911 A | 6/1989 |
| JP | 11510473 T | 9/1999 |

(Continued)

OTHER PUBLICATIONS

Udenigwe et al., "Potential of Resveratrol in Anticancer and Anti-Inflammatory Therapy", Nutrition Reviews, Aug. 1, 2008, vol. 66(8):445-454.

Haigis et al., "Mammalian Sirtuins: Biological Insights and Disease Relevance", Annu. Rev. Pathol. Mech. Dis. 2010.5:253-295.

Lekli et al., "Redox Regulation of Stem Cell Mobilization", NRC Research Press, Can. J. Physiol Pharmacol. 87: 989-995 (2009).

Kelly, "A Review of the Sirtuin System, its Clinical Implications, and the Potential Role of Dietary Activators like Resveratrol: Part 1", Alternative Medicine Review, vol. 15, No. 3, pp. 245-263, Sep. 15, 2010.

Kelly, "A Review of the Sirtuin System, its Clinical Implications, and the Potential Role of Dietary Activators like Resveratrol: Part 2", Alternative Medicine Review, vol. 15, No. 4, pp. 313-328, Sep. 15, 2010.

(Continued)

*Primary Examiner* — Patrick Lewis

(74) *Attorney, Agent, or Firm* — Edell, Shapiro & Finnan, LLC

(57) ABSTRACT

A resveratrol-containing composition capable of providing a therapeutic benefit to a subject such as modulation of a biological activity, improving cell transplantation therapy, or improving macular degeneration or dystrophy treatments. The compositions comprise trans-resveratrol, a metal chelator, one or more additional antioxidants such as quercetin, gamma-tocotrienol, or apple polyphenols, allicin, and nucleotides.

20 Claims, No Drawings

(56) References Cited

U.S. PATENT DOCUMENTS

| | | |
|---|---|---|
| 2007/0116838 A1 | 5/2007 | Prakash et al. |
| 2007/0149466 A1 | 6/2007 | Milburn et al. |
| 2007/0248590 A1 | 10/2007 | Milne et al. |
| 2008/0050347 A1 | 2/2008 | Ichim |
| 2009/0169585 A1* | 7/2009 | Sardi ............... A61K 31/05 424/400 |
| 2009/0226547 A1 | 9/2009 | Gilbard et al. |
| 2011/0009496 A1 | 1/2011 | Lunsmann et al. |
| 2011/0082189 A1 | 4/2011 | Sinclair et al. |
| 2012/0058088 A1 | 3/2012 | Sardi |

FOREIGN PATENT DOCUMENTS

| | | |
|---|---|---|
| JP | 2001506579 A | 5/2001 |
| JP | 2001519791 A | 10/2001 |
| JP | 2003119127 A | 4/2003 |
| JP | 2003517831 A | 6/2003 |
| WO | 9902158 A1 | 1/1999 |
| WO | 0006171 A1 | 2/2000 |
| WO | 03013566 A1 | 2/2003 |
| WO | 2005099761 A1 | 10/2005 |
| WO | 2006076681 A2 | 7/2006 |
| WO | 2006078941 A2 | 7/2006 |
| WO | 2006079021 A2 | 7/2006 |
| WO | 2006094209 A2 | 9/2006 |
| WO | 2006094210 A2 | 9/2006 |
| WO | 2006094233 A1 | 9/2006 |
| WO | 2006094235 A1 | 9/2006 |
| WO | 2006094236 A1 | 9/2006 |
| WO | 2006094237 A2 | 9/2006 |
| WO | 2006094239 A2 | 9/2006 |
| WO | 2006094246 A2 | 9/2006 |
| WO | 2006094248 A1 | 9/2006 |
| WO | 2006105403 A2 | 10/2006 |
| WO | 2006105440 A2 | 10/2006 |
| WO | 2006127987 A2 | 11/2006 |
| WO | 2007008548 A2 | 1/2007 |
| WO | 2007019344 A1 | 2/2007 |
| WO | 2007019345 A1 | 2/2007 |
| WO | 2007019346 A1 | 2/2007 |
| WO | 2007019416 A1 | 2/2007 |
| WO | 2007019417 A1 | 2/2007 |
| WO | 2007064902 A2 | 6/2007 |
| WO | 2007102861 A2 | 9/2007 |
| WO | 2008027379 A2 | 3/2008 |
| WO | 2009039195 A1 | 3/2009 |

OTHER PUBLICATIONS

Mukherjee et al., "Dose-Dependency of Resveratrol in Providing Health Benefits", International Dose-Response Society, DOI: 10.2203/dose-response.09-015.Mukherjee, 23 pages, Mar. 18, 2010.
Das, Commentary on "Resveratrol commonly displays hormesis: Occurance and Biomedical Significance" by Calabrese et al., Human and Experimental Toxicology, 19(12) 1016-10-17, Dec. 29, 2010.
Calabrese et al., "Resveratrol Commonly Displays Hormesis: Occurance and Biomedical Significance", Human and Experimental Toxicology, 29(12) 980-1015, 2010.
Barger et al., "Short-Term Consumption of a Resveratrol-Containing Nutraceutical Mixture Mimics Gene Expression of Long-Term Caloric Restriction in Mouse Heart", Experimental Gerontology 43 (2008) 859-866.
Regev-Shoshani et al., "Glycosylation of Resveratrol Protects it from Enzymic Oxidation", 2003 Biochemical Society, Biochem. J. (2003) 374, 157-163.
International Search Report received in corresponding PCT/US12/65556 dated Mar. 19, 2013.
Fang et al., "Studies on Egg Lecithin-Ibuprofen Complex", Journal of Shenyang Pharmaceutical University, 2000, vol. 17(6): 398, Shenyang, Liaoning, China.
"Now the Power of Liquid is Within Your Grasp", Capsugel Library, 1999, 6 pages.
SIRT1, Fluorescent Activity Assay/Drug Discovery Kit—AK—555, pp. 1-8, (2010).
Cole, "Liquid Filled and Sealed Hard Gelatin Capsules," Capsugel Library, 1999, pp. 1-12.
Prokop, J. et al. (2006) "Resveratrol and Its Glycon Piceid Are Stable Polyphenois," J. Medicinal Food 9(1): 11-14.
Boulton et al., Fate of the Vlavonoid Quercetin in Human Cell Lines: Chemical Instability and Metabolism, Journal of Pharmacy and Pharmacology, vol. 51, No. 3, Mar. 1999, p. 353-359, Abstract provided (2 pgs).
Palma et al., Stability of Phenolic Compounds During Extraction with Superheated Solvents, Journal of Chromatography A, 921 (2001) 169-174.
Graf et al., Phytic Acid, The Journal of Biological Chemistry, vol. 262, No. 24, p. 11647-11650, 1987.

* cited by examiner

COMPOSITIONS CONTAINING RESVERATROL AND NUCLEOTIDES

CROSS-REFERENCE TO RELATED APPLICATIONS

This application is a divisional of U.S. patent application Ser. No. 13/679,299, entitled "Compositions Containing Resveratrol and Nucleotides" (filed Nov. 16, 2012), which claims priority to U.S. Application Ser. No. 61/560,482 (filed on Nov. 16, 2011; expired), all of which are herein incorporated by reference in their entirety.

BACKGROUND

Despite a high level of risk factors such as cholesterol, diabetes, hypertension and a high intake of saturated fat, French males display the lowest mortality rate from ischaemic heart disease and cardiovascular diseases in Western industrialized nations (36% lower than the USA and 39% lower than the UK). The so-called 'French Paradox' (a low mortality rate specifically from cardiovascular diseases) may be due mainly to the regular consumption of wine (Renaud, S. et al. (1998) Novartis Found. Symp. 216:208-222, 152-158).

Resveratrol (3,4',5-trihydroxy-trans-stilbene) is a naturally occurring phenolic compound found, for example in grape skins, that has been demonstrated to have beneficial properties relating to health of humans. In particular, resveratrol is believed to be beneficial to the functioning of the heart and in extending the life of human cells. Resveratrol, when used in dietary supplements, is generally produced as an alcohol extract from plant sources.

Calorie restricted diets have been shown to enhance survival and longevity by up-regulating survival/longevity genes or down-regulating genes whose expression enhances cellular damage. Mice have been used extensively as a model for genetic expression comparisons with humans. Without limitation, the validity of murine models to human gene expression reflects the fact that 98% of human and murine gene are homologous, and that mice and humans have about the same number of genes (e.g., approximately 30,000).

Despite the established benefits of a calorie restricted diet, the severity of the required dietary regime has limited adoption of this approach to increasing longevity. It would therefore be desirable to provide an alternative route to obtaining the benefits of calorie restriction that would avoid the need for dietary regulation and that would be amenable to widespread adoption. The present embodiments are directed to this and other needs.

SUMMARY OF THE INVENTION

Embodiments of the present embodiments provide a composition that comprises trans-resveratrol, a metal chelating agent, one or more additional antioxidants such as quercetin, gamma-tocotrienol, or apple polyphenols, allicin, and nucleotides, and methods of using the composition. The trans-resveratrol may be encapsulated to substantially preserve the biological activity of the composition from loss due to exposure of the trans-resveratrol to light or oxygen. Additional embodiments provide a method of protecting implanted stem cells by administering a composition that comprises trans-resveratrol, a metal chelating agent, one or more additional antioxidants such as quercetin, gamma-tocotrienol, or apple polyphenols, allicin, and nucleotides, in conjunction with or following stem cell implantation.

DETAILED DESCRIPTION

The present embodiments relate to a resveratrol-containing composition and especially a resveratrol-containing dietary composition (i.e., a composition amenable for oral ingestion by a recipient), and to methods of treatment and/or prophylaxis utilizing such compositions.

A. Compositions of the Present Embodiments

In a preferred embodiment, the composition comprises or consists essentially of one or more plant extracts comprising trans-resveratrol, a metal chelating agent, one or more additional antioxidants such as quercetin, gamma-tocotrienol, or apple polyphenols, allicin, and nucleotides. These compositions exhibit numerous benefits as compared to pure resveratrol alone. Preferred compositions comprise resveratrol (preferably, a composition dosage of from about 1 mg/kg of body weight to about 2 g/kg of body weight (more preferably from about 1 mg/kg of body weight to about 5 mg/kg of body weight), a chelator, and an antioxidant, and may also comprise other compounds such as emulsifiers, glycosaminoglycans, etc.

In a preferred embodiment, the composition is intended for a human, and comprises or consists essentially of (assuming a standard 50 kg patient):
  (a) trans-resveratrol in an amount of about 0.2-2 mg/kg, preferably about 0.5-1.5 mg/kg, or about 1 mg/kg of body weight of the patient;
  (b) a chelator such as phytic acid in an amount of about 0.5-3 mg/kg, about 1.25-3 mg/kg, or about 3 mg/kg of body weight of the patient;
  (c) additional phenolic antioxidants such as quercetin and apple polyphenols (e.g., procyanidin B-2) in a total amount of about 0.05-2 mg/kg, about 0.2-1.5 mg/kg, or about 0.5 mg/kg of body weight of the patient;
  (d) tocotrienols particularly gamma-tocotrienol in an amount of about 0.03-0.3 mg/kg, about 0.1-0.2 mg/kg, or about 0.12 mg/kg of body weight of the patient;
  (e) allicin in an amount of about 0.5-2 mg/kg, about 0.75-1.5 mg/kg, or about 1 mg/kg of body weight of the patient; and
  (f) nucleotides in an amount of about 0.5-2 mg/kg, about 0.75-1.5 mg/kg, or about 1 mg/kg of body weight of the patient.

In another preferred embodiment, the composition is intended for a human, and comprises or consists essentially of:
  (a) trans-resveratrol in an amount of about 10-100 mg, preferably about 50-75 mg, or about 50 mg;
  (b) a chelator such as phytic acid in an amount of about 25-150 mg, about 75-150 mg, or about 150 mg;
  (c) additional phenolic antioxidants such as quercetin and apple polyphenols (e.g., procyanidin B-2) in a total amount of about 2.5-75 mg, about 10-75 mg, or about 25 mg;
  (d) tocotrienols particularly gamma-tocotrienol in an amount of about 1.5-15 mg, about 5-10 mg, or about 6 mg;
  (e) allicin in an amount of about 25-100 mg, about 37.5 to 75 mg, or about 50 mg; and
  (f) nucleotides in an amount of about 25-100 mg, about 37.5 to 75 mg, or about 50 mg.

In a preferred embodiment, the composition comprises resveratrol and is sold commercially as Longevinex® (Resveratrol Partners, LLC, San Dimas, Calif.). Four different formulations of Longevinex® have been sold, each consisting essentially of a plant extract comprising trans-resveratrol, quercetin dihydrate, and rice bran extract comprising phytic acid. Each dose of Longevinex® is suitable for administration to an average (e.g., 70 kg) human once daily. Each dose (e.g., a capsule) of the first generation Longevinex® composition consists essentially of: 5 mg Vitamin E (as mixed tocopherols), 215 mg of a mixture of *Vitis vinifera* (French red wine grape) and *Polygonum cuspidatum* (giant knotweed) extracts together comprising 100 mg of trans-resveratrol, 25 mg quercetin dihydrate, 75 mg rice bran extract comprising phytic acid, 380 mg rice bran oil comprising ferulic acid, and 55 mg sunflower lecithin. Each dose (e.g., a capsule) of the second generation Longevinex® composition consists essentially of: 215 mg of a mixture of *Vitis vinifera* (French red wine grape) and *Polygonm cuspidatum* (giant knotweed) extracts together comprising 100 mg of trans-resveratrol, 25 mg quercetin dihydrate, 75 mg rice bran extract comprising phytic acid, and 50 mg ferulate. Each dose (e.g., two capsules) of the third generation Longevinex® consists essentially of a *Polygonum cuspidatum* extract comprising 100 mg of trans-resveratrol, 1000 IU of cholecaliferol (Vitamin D3), quercetin, and rice bran extract comprising phytic acid. Each dose (e.g., two capsules) of the fourth generation Longevinex®, sold as Longevinex Advantage™, consists essentially of a *Polygonum cuspidatum* extract comprising 100 mg of trans-resveratrol, 1000 IU of cholecaliferol (Vitamin D3), grape seed extract, quercetin, ferulic acid, cocoa extract, lutein, green tea extract, rice bran extract comprising phytic acid, and hyaluronan.

1. Resveratrol

Resveratrol has been ascribed multiple beneficial biological effects (see, e.g., U.S. Pat. No. 7,345,178, which listing of disclosed effects is herein incorporated by reference), including preventing or treating cardiovascular disease, preventing or treating cancer, preventing or treating macular degeneration, attenuating or preventing diseases associated with aging, and other conditions and illnesses, including the incidence or severity of neurodegenerative diseases such as Alzheimer's Disease and Parkinson's Disease, and anti-inflammatory activity.

Resveratrol, also known as 3,4',5 trihydroxystilbene, naturally exists in cis- and trans-stereoisomeric forms. Studies have shown that resveratrol is biologically active, providing several health benefits including cancer prevention, anti-inflammatory properties, and cardiovascular effects. To maintain biological activity for an "extended period" of time, the small molecules of plant or synthetic source preferably remain biologically active for time periods after which the molecules would naturally become biologically inactive due to degradation or molecular isomerization as a result of exposure to light, heat or oxygen. These destructive processes would likely occur during extraction, encapsulation or storage. For example, resveratrol possesses a half-life of approximately one day; consequently, it typically loses significant biological activity within two days of exposure to ambient conditions and during processing of dietary supplements. Preferably, the resveratrol used in the present compositions is entirely or primarily (e.g., more than 75, 80, 85, 90, or 95%) in the trans stereoisomeric form, i.e., trans-resveratrol.

Resveratrol may be synthesized chemically, or, more preferably, may be extracted from plant sources. Resveratrol is found in at least 72 species of plants distributed among 31 genera and 12 families. All of the families found to contain resveratrol belong to the spermatophytes division: Vitaceae, Myrtaceae, Dipterocarpaceae, Cyperaceae, Gnetaceae, Leguminosae, Pinaceae, Moraceae, Fagaceae, Liliaceae. Resveratrol has most often been reported in non-edible plants: vine, eucalyptus, spruce, and the tropical deciduous tree *Bauhinia racemosa, Pterolobium Hexapetallum*. Resveratrol is particularly found in grape skins and Giant Knotweed, cocoa and chocolate. Peanut sprouts are also a rich source of resveratrol.

In a preferred embodiment, the resveratrol is naturally derived, i.e., derived from at least one natural source such as plants (or parts thereof, such as tubers or fruit (including pulp and skins) from the plant). One preferred source is the seeds and/or skins of grapes, such as *Vitis vinifera, Vitis labrusca*, and *Vitis rotundifolia*. Another preferred source is *Polygonum* (Giant Knotweed) and, in particular, *Polygonum cuspidatum* (a species of giant knotweed). The natural derivation process includes those processes generally known in the art, including an extraction process in which a solvent is used to extract the small molecules from a natural source. The solvent includes aqueous solvents, organic solvents, and mixtures thereof. The solvent may include, but is not limited to, alcohols such as ethanol. By way of specific examples, the extracted material may include aqueous or organic solvent extracts of plants (or parts thereof), fruit juices (e.g., grape juice), and fermented liquors (e.g. wine) produced from plants or fruit juice, or mixtures of any of the foregoing. The extracted material may further include inert plant material naturally removed during the extraction process. The extracted material may be processed (physically and/or chemically) to remove the solvent and increase the concentration of the small molecules. For example, the solvent may be removed from the extract (e.g., by drying), leaving a dried powder.

In a preferred embodiment, the compositions comprise or consist essentially of a plant extract comprising trans-resveratrol, for example, a plant (grape) extract from *Vitis vinifera, Vitis labrusca*, or *Vitis rotundifolia*, a plant extract from a *Polygonum* species, or a combination of grape and/or *Polygonum* extracts. In a preferred embodiment, the compositions comprise or consist essentially of a mixture of grape and *Polygonum* extracts, each comprising trans-resveratrol. In one embodiment, a *Polygonum cuspidatam* extract containing 8% resveratrol (98% in trans-resveratrol form) from Blue California (Rancho Santa Margarita, Calif.) is used. As used herein, the term "extract" or "plant extract" has its ordinary meaning of a concentrated pharmaceutical preparation of a plant obtained by removing active constituents (such as trans-resveratrol) with a suitable solvent or menstruum, which is evaporated away or otherwise removed to yield a residual mass of plant extract. The extract may be adjusted to a prescribed standard. Thus, it is understood by those skilled in the art that an "extract" or "plant extract" is not simply a pure active ingredient or ingredients, but instead contains secondary material from the source plant, for example, depending on the source plant, organic and inorganic salts, organic bases and acids, saponins, polyphenols, tannins, sugars, polysaccharides, etc.

In a preferred embodiment, trans-resveratrol is present in the composition in an amount of about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 percent by weight, or is present in any range between any two of these amounts, e.g., between about 10 and 30%, in an amount lesser than or greater than any two of these amounts, e.g. lesser than 15% or greater than 75%, or in an amount lesser than or equal to, or greater than or equal to any two of these amounts, e.g., lesser than or equal to 15%. In a different preferred embodiment, the trans-resveratrol is present in the composition in an amount of about 5-50%, 7.5-45%, 10-40%, 12.5-35%, 15-30%, or 20-25% by weight. In another preferred embodiment, trans-resveratrol is present in the composition in an amount of about 5-30% or 10-20% by weight. In a different preferred embodiment, trans-resveratrol is present in the composition in an amount of about 10-35%, 12.5-30%, or 15-25%, or in an amount of about 15-35% or 20-30% by weight.

In a preferred embodiment, trans-resveratrol is present in the composition in an amount calculated to provide a dosage in milligrams trans-resveratrol per kilogram of the patient to whom the dosage will be administered, for example, in an amount of about 0.25, 0.5, 0.75, 1, 1.25, 1.5, 1.75, 2, 2.25, 2.5, 2.75, 3, 3.25, 3.5, 3.75, 4, 4.25, 4.5, 4.75 or 5 mg trans-resveratrol per kilogram of patient, which is equivalent to a dosage of about 17.5, 35, 52.5, 70, 87.5, 105, 122.5, 140, 157.5, 175, 192.5, 210, 227.5, 245, 262.5, 280, 297.5, 315, 332.5, or 350 mg trans-resveratrol for the typical 70 kg human patient. In another preferred embodiment, trans-resveratrol is present in the composition in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg trans-resveratrol per kilogram of patient, or about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mg trans-resveratrol per kilogram of patient. The trans-resveratrol may also be present in any range between any two of these amounts, e.g., between about 0.25 and 4 mg/kg or between about 26 and 33 mg/kg, in an amount lesser than any of these amounts, e.g., lesser than about 2.5 mg/kg or 50 mg/kg, in an amount lesser than or equal to any of these amounts, e.g., lesser than or equal to about 50 mg/kg, in an amount greater than any of these amounts, e.g., greater than about 1.25 mg/kg or 25 mg/kg, or in an amount greater than or equal to any of these amounts, e.g., greater than or equal to about 2.5 mg/kg or 100 mg/kg. In a preferred embodiment, trans-resveratrol is present in the composition in an amount of about 1.5 to about 2.5 mg/kg for a human patient, or about 3 to about 4.5 mg/kg for a human patient.

2. Chelators

As used herein the term "chelator" refers to an organic compound that bonds with and removes free metal ions from solution. Examples of suitable chelators include ethylenediaminetetraacetic acid (EDTA), histidine, antibiotic drugs of the tetracycline family, pyridoxal 2-chlorobenzoyl hydrazone, desferrioxamine, dexrazoxane, deferasirox, pyoverdine, pseudan, citrate, NDGA (nordihydroguaiaretic acid: 1,4-bis[3,4-dihydroxyphenyl]2,3-dimethylbutane), ferulic acid and phytic acid. Preferably, the compositions of the present embodiments will provide a composition dosage of chelator of from about 1 g to about 15 g, more preferably from about 2 g to about 12 g.

Phytic acid is a particularly preferred chelator for the purposes of the present embodiments. As used herein, the term "phytic acid" refers to inositol hexaphosphate ((2,3,4,5,6-pentaphosphonooxycyclohexyl)dihydrogen phosphate; also known as "IP6"). Phytic acid is found in substantial amounts in whole grains, cereals, legumes, nuts, and seeds, and is the primary energy source for the germinating plant. Phytic acid and its lower phosphorylated forms (such as IP3) are also found in most mammalian cells, where they assist in regulating a variety of important cellular functions. Phytic acid is preferably provided in the form of a rice bran extract comprising phytic acid. Phytic acid is reported to function as an antioxidant by chelating divalent cations such as copper and iron, thereby preventing the generation of reactive oxygen species responsible for cell injury and carcinogenesis. The preferred composition dosage of phytic acid (for example, as derived from rice bran as an extract) is in the range of 200-12,000 mg, more preferably about 250-2500 mg per day.

Phytic acid also is believed to reduce the availability of metallic minerals that serve as growth factors in tumor cells, and as an inhibitor of calcium cystallization. It is also believed to serve as a neutrophil priming and motility agent. Additionally, phytic acid has been found to be neuroprotective, and thus to attenuate the severity of conditions associated with neurodegenerative diseases (especially Parkinson's Disease, camptocormia, and Alzheimer's Disease). The components of the present compositions are believed to enhance such neuroprotection.

The chelator may be of natural or synthetic source and may include, but not be limited to synthetic chelators such as desferrioxamine, EDTA, and d-penicillamine, or natural chelators such as lactoferrin, inositol hexaphosphate (IP6), quercetin, catechin, ferulic acid, curcumin, ellagic acid, hydroxytyrosol, anthocyanidin, etc. A preferred source of IP6 is a rice bran extract from Tsuno Rice Fine Chemicals Co., Ltd. of Japan, although the IP6 may also be used in isolated form In a preferred embodiment, a chelator is present in the composition in an amount of about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 percent by weight, or in an amount of about 0.25, 0.5, 0.75, 1, 1.25, 1.5, 1.75, 2, 2.25, 2.5, 2.75, 3, 3.25, 3.5, 3.75, 4, 4.25, 4.5, 4.75 or 5 mg chelator per kilogram of patient, or is present in any range between any two of these amounts, in an amount lesser than or greater than any two of these amounts, or in an amount lesser than or equal to, or greater than or equal to any two of these amounts. In a preferred embodiment, the chelator is present in the composition in an amount of about 10 to 35%, 15 to 30%, 20 to 30%, or 17.5 to 27.5%, or in amount of about 0.5 to 1.5 mg/kg of patient, 0.75 to 1.25 mg/kg of patient, or about 1 mg/kg of patient.

3. Additional Antioxidants

Additional antioxidants, for example phenolic antioxidants, tocotrienols, or Vitamin D may be added to the compositions. The additional phenolic antioxidants may be, for example, quercetin, ferulic acid, butein, fisetin, myricetin, kaempferol, cis-resveratrol or piceatannol, or for example, apple polyphenols such as procyanidins, phenol carboxylic acids, catechins, flavonoids and others. The antioxidants are believed to provide improved bioavailability of resveratrol by inhibiting resveratrol glucuronidation, and also act synergistically with resveratrol or independently of resveratrol to provide beneficial function.

The additional phenolic antioxidants may belong to a number of chemical classes of phenolic antioxidant compounds, such as the chalcones (e.g., butein), the flavonoids, the hydroxycinnamic acids, and the stilbenoids (e.g., cis-resveratrol, piceatannol). The flavonoids are a large class of phenolic compounds including the flavanols (2-phenyl-3,4-dihydro-2H-chromen-3-ols such as the catechins and epicatechins), the flavones (2-phenylchromen-4-ones such as apigenin), and the flavonols (3-hydroxy-2-phenylchromen-4-ones such as quercetin).

In one embodiment, the additional phenolic antioxidant comprises or consists of an antioxidant chalcone such as butein. In another embodiment, the additional phenolic antioxidant comprises or consists of a hydroxycinnamic acid selected from the group consisting of caffeic acid, cichoric acid, chlorogenic acid, caftaric acid, coumaric acid, coutaric acid, diferulic acids, fertaric acid, and ferulic acid, or combinations thereof. In a preferred embodiment, the additional phenolic antioxidant comprises or consists of a combination of caffeic acid and ferulic acid. In yet another embodiment, the additional phenolic antioxidant comprises or consists of a stilbenoid selected from the group consisting of cis-resveratrol and piceatannol.

In a further embodiment, the additional phenolic antioxidant comprises or consists of a flavanol selected from the group consisting of catechin (C), catechin 3-gallate (CG), epicatechin (EC), epicatechin 3-gallate (ECG), epigallocatechin (EGC), epigallocatechin 3-gallate (EGCG), gallocatechin (GC), and gallocatechin 3-gallate (GCG), or combinations thereof. In a preferred embodiment, the additional phenolic antioxidant comprises or consists of epigallocatechin 3-gallate (EGCG). In another embodiment, the additional phenolic antioxidant comprises or consists of a flavone selected from the group consisting of apigenin, baicalein, chrysin, diosmin, luteolin, scutellarein, tangeritin, and wogonin, or combinations thereof. In a preferred embodiment, the additional phenolic antioxidant comprises or consists of apigenin. In yet another embodiment, the additional phenolic antioxidant comprises or consists of a flavonol selected from the group consisting of quercetin, kaempferol, myricetin, fisetin, isorhamnetin, pachypodol, and rhamnazin, or combinations thereof.

In a further embodiment, the additional phenolic antioxidant comprises or consists of one or more apple polyphenols selected from the group consisting of procyanidins, phenol carboxylic acids, catechins, and flavonoids. The procyanidins are a class of flavanols also called proanthocyanidins, leukocyanidins, or condensed tannins. They are antioxidants linked to reduced risk of coronary heart disease and to lower overall mortality, and to the stabilization of collagen and maintenance of elastin. Preferably, the apple polyphenols comprise or consist essentially of procyanidins, such as the dimeric B type procyanidins proanthocyanidin B1 [epicatechin-(4β→8)-catechin], proanthocyanidin B2 [(−)-epicatechin-(4β→8)-(−)-epicatechin], proanthocyanidin B3 [catechin-(4β→8)-catechin], and proanthocyanidin B4 [catechin-(4α→8)-epicatechin]. Preferably, the procyanidin is procyanidin B2. In one embodiment, an apple (*Malus pumila*) extract from Blue California (Rancho Santa Margarita, Calif.) is used, for example the 10% or 40% polyphenol apple extracts.

In a further embodiment, the additional phenolic antioxidant comprises or consists of one or more tocotrienols. The tocotrienols may be any mix of alpha, beta, gamma and delta tocotrienols, preferably gamma tocotrienols. They may be present as isolated tocotrienols, or as part of a plant extract, e.g., an extract from palm, wheat germ, sunflowers, safflowers, etc. A preferred source of tocotrienols is from Davos Life Science.

The additional phenolic antioxidant may also comprise or consist of a combination of phenolic antioxidants, for example one or more flavonoids combined with one or hydroxycinnamic acids, etc. In one embodiment, the additional phenolic antioxidant comprises or consists of a combination of apigenin, caffeic acid, EGCG, ferulic acid, and quercetin. In another embodiment, the additional phenolic antioxidant comprises or consists of a combination of quercetin and one or more apple polyphenols.

In a preferred embodiment, one or more additional phenolic antioxidants and/or tocotrienols are present in the composition in an amount of about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 percent by weight, or in an amount of about 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 mg additional phenolic antioxidant per kilogram of patient, or is present in any range between any two of these amounts, in an amount lesser than or greater than any two of these amounts, or in an amount lesser than or equal to, or greater than or equal to any two of these amounts. In a preferred embodiment, the one or more additional phenolic antioxidants are present in the composition in an amount of about 1 to 25%, 2.5 to 20%, 5 to 15%, or 7.5 to 12.5%, or in an amount of about 5-10%, or in an amount of about 0.05 to 2, about 0.1 to 1.5, or about 0.15 to 1 mg/kg of patient, or in an amount of about 0.15 to about 6, about 0.3 to 4.5, or about 0.45 to 3 mg/kg of patient.

A non-phenolic antioxidant such as vitamin D may also be present in the compositions. As used herein, the term "Vitamin D" refers to a fat-soluble prohormone. Two major forms of vitamin D are vitamin $D_2$ (ergocalciferol) and vitamin $D_3$ (cholecalciferol) (DeLuca, H. F. et al. (1998) Nutr. Rev. 56:S4-S10). Vitamin D exhibits many biological actions. While vitamin D is widely known for its ability to stave off bone disease (rickets in growing children, osteoporosis in senior adults), it is becoming a central player in the battle against cancer. Regarding the role of vitamin D in immunity and cancer, vitamin D improves the chemotactic (affinity for) neutrophils to mobilize and migrate. Patients with rickets due to vitamin D deficiency are observed to have sluggish neutrophils that cannot migrate properly. Vitamin D stimulates the maturation of monocytes to macrophages. This results in an enlarged army of immune fighting cells to mount against tumors. Vitamin D is widely available commercially, and such preparations are suitable for the purposes of the present embodiments. Preferably, the compositions of the present embodiments will provide a composition dosage of vitamin D of from about 100 IU to about 100,000 IU, more preferably from about 1,000 IU to about 50,000 IU.

Vitamin D3 works as an agent that mimics the response to a biological stressor, solar radiation. In particular, vitamin D3 upregulates protective genes involved in activation of the immune system, particularly neutrophil count and motility, and aids in overcoming the decline in endogenous vitamin D3 production with advancing age due to thickening of the skin, which reduces sun/skin production of vitamin D. Furthermore, vitamin D3 works synergistically to breakdown IP6 to IP3, thought to be a major active molecule. Resveratrol also works synergistically to sensitize cells to vitamin D3 (sensitizes the vitamin D receptor on the cell surface). Vitamin D serves to break down IP6 to IP3, which is its primary active form. Vitamin D is also believed to act as an immune system enhancing agent, boosting innate immunity in humans. In this capacity, vitamin D has been shown experimentally to have important cancer-preventive and cancer-curing properties. Resveratrol increases the sensitivity of the vitamin D receptor on the surface of cells, and thus is believed to act as an enhancing agent for vitamin D and as an anti-cancer agent. Resveratrol up-regulates the vitamin D receptor on the surface of healthy and cancer cells, and sensitizes cancer cells to vitamin D. Resveratrol is also believed to be a monoamine oxidase inhibitor (MAO Inhibitor).

In a preferred embodiment, Vitamin D is present in the composition in an amount of about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 percent by weight, or in an amount of about 0.25, 0.5, 0.75, 1, 1.25, 1.5, 1.75, 2, 2.25, 2.5, 2.75, 3, 3.25, 3.5, 3.75, 4, 4.25, 4.5, 4.75 or 5 micrograms (µg) Vitamin D per kilogram of patient, or in an amount of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900 or 3000 micrograms (µg) Vitamin D per kilogram of patient. Vitamin D may also be present in an amount of about 50-150,000 IU, about 100-100,000 IU, or about 1000 to 50,000 IU, where 1 microgram (µg) Vitamin D is equivalent to 40 IU. Vitamin D may also be present in any range between any two of these amounts, in an amount lesser than or greater than any two of these amounts, or in an amount lesser than or equal to, or greater than or equal to any two of these amounts. In a preferred embodiment, Vitamin D is present in the composition in an amount of about 2.5 to 2500 micrograms/kg of patient, or about 25 to 1250 micrograms/kg of patient.

4. Nucleotides

The compositions of the present embodiments may also contain nucleotides or related compounds such as nucleotide salts, nucleosides, nucleobases, whole RNA, and the like. For example, in a preferred embodiment, the compositions may contain one or more ribonucleotides such as adenosine monophosphate, cytidine monophosphate, guanosine monophosphate, inosine monophosphate, ribothymidine monophosphate, and uridine monophosphate, and/or one or more deoxyribonucleotides such as deoxyadenosine monophosphate, deoxycytidine monophosphate, deoxyguanosine monophosphate, deoxyinosine monophosphate, deoxythymidine monophosphate, and deoxyuridine monophosphate.

The related compounds are compounds that are precursors of nucleotides (e.g., nucleosides or nucleobases), derivatives of nucleotides (e.g., nucleotide salts, nucleoside diphosphates, nucleoside triphosphates), or compositions comprising nucleotides such as DNA or RNA. In a preferred embodiment, the compositions may contain one or more ribonucleosides such as adenosine, cytidine, guanosine, inosine, ribothymidine and uridine, and/or one or more deoxyribonucleosides such as deoxyadenosine, deoxycytidine, deoxyguanosine, deoxyinosine, deoxythymidine and deoxyuridine. In a preferred embodiment, the compositions may contain RNA and/or DNA, which by their nature comprise a number of different nucleotides.

The compositions may contain isolated nucleotides or related compounds, or may contain extracts that are high in nucleotides. For example, in a preferred embodiment, the compositions comprise an extract high in nucleotides, such as an extract from the pea plant, green algae *Chlorella*, the brown algae Kelp, the cyanobacteria *Spirulina*, Brewer's Yeast, and fish oils (from, e.g., sardines, mackerel, etc.). In another preferred embodiment, the compositions comprise the nucleotides or related compounds in isolated form, for example as sourced from Lalilab, Inc.

Nucleotides have been demonstrated to affect immune functions, including the enhancement and modulation of T-cell function and maturation and NK cell activity, reversing immunosuppression caused by malnutrition and starvation, and increasing resistance to infectious agents such as *S. aureus* and *C. albicans*. Nucleotides have also been shown to stimulate tissue repair and intestinal repair. The mechanism by which nucleotides produce these effects is unclear, but it is possible that salvage of supplemental nucleotides utilizes less energy than de novo synthesis, thus allowing the body to devote more energy to immune function and tissue regeneration.

Other benefits include enhanced DNA repair via adding to the nucleotide pool (spare parts pool), reduction in DNA mutations (particularly substitutions of incorrect nucleotides), more rapid immune response with provision of nucleotides to form new white blood cells, particularly fast-responding neutrophils, enhanced wound repair, and reduced risk of pre-cancerous tissues (neoplasia, hyperplasia). Another benefit is improved cell turnover rate in tissues where there is characteristically slow cell turnover rate, such as in brain, heart and eyes, which is particularly desirable in brain following stroke and heart following a heart attack. Further benefits include reduction in fibrosis (tissue scarring), and improved stem cell regeneration.

5. Other Components

The compositions of the present embodiments may contain additional components, including additional active components that act to enhance resveratrol biological activity and inactive compounds (e.g., flavorants, sweeteners, dyes, vitamins, amino acids (e.g., lysine, proline, etc.), minerals, nutrients, etc.). For example, tocopherols such as Vitamin E, sunflower lecithin, grape seed extract, cocoa extract, lutein, and green tea extract are preferred additional components in certain embodiments. Emulsifiers, fillers, binding agents, and the like may also be included in the compositions of the present embodiments.

In a preferred embodiment, allicin is an additional component. Allicin is an organosulfur compound isolated from garlic that has antibacterial and anti-fungal properties. Several animal studies published between 1995 and 2005 indicate that allicin may: reduce atherosclerosis and fat deposition, normalize the lipoprotein balance, decrease blood pressure, have anti-thrombotic and anti-inflammatory activities, and function as an antioxidant to some extent. Allicin may be used in isolated form, or as a garlic extract such as Garli-Eze® garlic extract sold by Nutra Products, Inc.

The combination of the present embodiments is intended for human or animal oral intake as a dietary supplement. For example, such compositions may comprise a combination of resveratrol and hyaluronan in a dietary supplement that serves to heal a variety of illnesses including some cancers. Resveratrol is known to be an anti-cancer molecule and to have other healing and longevity enhancing properties. Hyaluronan (hyaluronic acid, HA) is taken as an oral supplement or can be given intravenously to target cancer cells. When combined with or attached to other molecules, hyaluronan will deliver other anti-cancer and healing agents such as resveratrol to tumor sites. The combination may or may not include a chelating agent, an antioxidant and/or an emulsifier. When encapsulated or otherwise applied together, with or without those additives, resveratrol and HA have powerful healing properties for animals and humans.

Most preferably, the compositions of the present embodiments stabilize resveratrol specific activity such that the resveratrol of the compositions has a specific activity that is greater than that of resveratrol maintained in the presence of oxygen gas, or maintained in the absence of a chelator, hyaluronic acid, or vitamin D. Preferably, the amounts of the non-resveratrol constituents of the compositions will stabilize the composition's resveratrol so that it exhibits at least 10% more activity, at least 20% more activity, at least 50% more activity, at least 2-times the activity, at least 5-times the activity, or at least 10-times the activity of resveratrol maintained in the presence of oxygen gas, or maintained in the absence of a chelator, hyaluronic acid, or vitamin D and so that it remains capable of exhibiting such specific activity over extended periods (for example, 1, 2, 4, 6, 10, 12, 18, 24, or 36 months or longer) at ambient conditions of temperature and humidity (i.e., without need for special precautions as to temperature or humidity).

In a preferred embodiment, the composition comprises or consists essentially of one or more plant extracts comprising trans-resveratrol and one or more of the following: a chelator such as phytic acid; one or more additional phenolic antioxidants such as quercetin or ferulic acid (ferulate); and Vitamin D. These compositions exhibit numerous benefits as compared to pure resveratrol alone. A particular benefit, explained in detail in Example 6 below, is that the present compositions do not exhibit the hormetic action characteristic of resveratrol (a dose-response relationship that is stimulatory at low doses, but detrimental at higher doses resulting in a J-shaped or an inverted U-shaped dose response curve). Instead, the present compositions have an L-shaped dose response curve, meaning that they are safe (non-toxic) even at high doses.

Preferred compositions comprise resveratrol (preferably, a composition dosage of from about 10 mg to about 2 g, more preferably from about 100 mg to about 500 mg), and at least one compound selected from the group consisting of an chelator, a glycosaminoglycan (e.g., hyaluronic acid), and vitamin D, and may also comprise other compounds such as antioxidants, emulsifiers, etc.

B. Methods of Treatment

The administration of the compositions of the present invention may be for a "prophylactic" or "therapeutic" purpose. The compositions of the present invention are said to be administered for a "therapeutic" purpose if the amount administered is physiologically significant to provide a therapy for an actual manifestation of the disease. When provided therapeutically, the composition is preferably provided at (or shortly after) the identification of a symptom of actual disease. The therapeutic administration of the compound serves to attenuate the severity of such disease or to reverse its progress. The compositions of the present invention are said to be administered for a "prophylactic" purpose if the amount administered is physiologically significant to provide a therapy for a potential disease or condition, e.g., to reduce the risk of heart attacks, to maintain health, to sustain a youthful appearance, to sustain function (e.g., to sustain a certain level of visual acuity, etc. When provided prophylactically, the composition is preferably provided in advance of any symptom thereof. The prophylactic administration of the composition serves to prevent or attenuate any subsequent advance of the disease.

Providing a therapy or "treating" refers to any indicia of success in the treatment or amelioration of an injury, pathology or condition, including any objective or subjective parameter such as abatement, remission, diminishing of symptoms or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, neuropsychiatric examination, and/or laboratory methods.

Preferred subjects for treatment include animals, most preferably mammalian species such as humans, and domestic animals such as dogs, cats and the like, subject to disease and other pathological conditions. A "patient" refers to a subject, preferably mammalian (including human). In a preferred embodiment, the subject or patient is a human, and in a more preferred embodiment, the subject or patient is a human having or at risk of developing one or more of cardiovascular disease, cancer, macular degeneration, aging, neurodegenerative diseases (e.g., Alzheimer's Disease, Parkinson's Disease, etc.) and inflammation.

A variety of administration routes for the compositions of the present invention are available. The particular mode selected will depend, of course, upon the particular therapeutic agent selected, whether the administration is for prevention, diagnosis, or treatment of disease, the severity of the medical disorder being treated and dosage required for therapeutic efficacy. The methods of the present embodiments may be practiced using any mode of administration that is medically acceptable, and produces effective levels of the active compounds without causing clinically unacceptable adverse effects. Such modes of administration include, but are not limited to, oral, buccal, sublingual, inhalation, mucosal, rectal, intranasal, topical, ocular, periocular, intraocular, transdermal, subcutaneous, intra-arterial, intravenous, intramuscular, parenteral, or infusion methodologies. In a preferred embodiment, administration is oral.

The dosage schedule and amounts effective for therapeutic and prophylactic uses, i.e., the "dosing regimen", will depend upon a variety of factors, including the stage of the disease or condition, the severity of the disease or condition, the general state of the patient's health, the patient's physical status, age and the like. In calculating the dosage regimen for a patient, the mode of administration also is taken into consideration. The dosage regimen also takes into consideration pharmacokinetics parameters well known in the art, i.e., the rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108). The state of the art allows the clinician to determine the dosage regimen for each individual patient, therapeutic agent and disease or condition treated. Single or multiple administrations of the compositions of the present invention can be administered depending on the dosage and frequency as required and tolerated by the patient. The duration of prophylactic and therapeutic treatment will vary depending on the particular disease or condition being treated. Some diseases lend themselves to acute treatment whereas others require long-term therapy.

The compositions of the present embodiments may be administered to a subject alone, or to a subject who is or will receive another medicament or medical therapy. For example, in a preferred embodiment, the compositions of the present embodiments are co-administered to a subject with stem cell therapy or a treatment for macular degeneration or macular dystrophy. Co-administration may be simultaneous, serially, contemporaneously, or in any other suitable fashion.

In a preferred embodiment, said administration or co-administration provides a therapeutic or prophylactic benefit to the subject that is at least 1.5 fold, 2 fold, 2.5 fold, 3 fold, 3.5 fold, 4 fold, 4.5 fold, 5 fold, 5.5 fold, 6 fold, 6.5 fold, 7 fold, or more than 7 fold greater than the therapeutic or prophylactic benefit achieved by resveratrol alone, calorie restriction alone, or the other medicament or medical therapy (e.g., stem cell therapy or treatment of macular degeneration or macular dystrophy) alone. In another preferred embodiment, said co-administration provides a therapeutic or prophylactic benefit to the subject that is at least 125 percent, 150 percent, 175 percent, 200 percent, 250 percent, 300 percent, 350 percent, 400 percent, 450 percent, 500 percent, or more than 500 percent greater than the therapeutic or prophylactic benefit achieved by resveratrol alone, calorie restriction alone, or the stem cell therapy or treatment of macular degeneration or macular dystrophy alone.

The compositions of these embodiments enhance resveratrol's specific activity. The compositions of the present embodiments therefore find utility in the treatment or prophylaxis of diseases (or in the amelioration of the symptoms of diseases) such as cardiovascular disease, cancer, macular degeneration, aging, neurodegenerative diseases (e.g., Alzheimer's Disease, Parkinson's Disease, etc.) and inflammation in which the modulation of expression of "survival/longevity" genes and/or "damage inducing" genes is desired. Over time, as minerals such as calcium and iron accumulate in the human body, genes respond in deleterious ways. Liu, Y. et al. (2005) Ann. Clin. Lab. Sci. 35(3):230-239; Templeton, D. M. et al. (2003) Biochim. Biophys. Acta. 1619(2):113-124; Ikeda, H. et al. (1992) Hepatology 15(2):282-287. The present embodiments have particular utility in the treatment of macular degeneration, cancer and the conditions of aging.

Additional embodiments provide a method of ameliorating a symptom associated with an existing disease of an individual or for preventing the onset of the symptom in an individual prior to the occurrence of the disease in the individual, which comprises administering to the individual, a resveratrol-containing composition that modulates the concentration or activity, relative to resveratrol alone or calorie restriction, of the product of a survival/longevity gene or the product of a gene whose expression enhances cellular damage, wherein the resveratrol is provided in an amount effective to cause a modulation of the concentration or activity of the gene that ameliorates the symptom of the disease, and wherein the disease is selected from the group consisting of: cardiovascular disease, cancer, macular degeneration, a disease associated with aging, and inflammation. The embodiments further provide such methods wherein the disease is cancer, or a disease associated with aging (especially a neurodegenerative disease).

1. Stem-Cell-Related Methods

In one preferred embodiment, the compositions of the present embodiments are co-administered to a subject with cell implantation or transplant therapy such as stem cell implantation or injection. The cells may be stem cells or cells derived from stem cells, such as human embryonic stem cells, or adult stem cells such as bone marrow stem cells, cardiac stem cells, endothelial stem cells, hematopoietic stem cells, mammary stem cells, mesenchymal stem cells, neural crest stem cells, neural stem cells, olfactory adult stem cells, testicular stem cells, and very small embryonic-like "VSEL" stem cells, or combinations thereof, or cells derived from any of the foregoing. In a preferred embodiment, the transplanted cells are selected from the group consisting of cardiac stem cells, neural stem cells, and retinal pigment epithelial (RPE) cells.

The therapeutic benefits that may be shown in such cell transplant-related embodiments include one or more benefits selected from the group consisting of improved stem cell differentiation, improved cell adhesion, improved cell survival, improved cell proliferation, and combinations thereof.

Stem cells are recognized as the origin of all renewed cells in the human body. Stem cell implantation is believed to be of benefit in regeneration of damaged tissues, particularly for brain or heart tissue damaged by infarction or trauma, or tissue that does not normally exhibit rapid cell renewal and turnover. Chacko et al., Am. J. Physiol. Heart Circ. Physiol. 2009 396(5):H1263-73; Wakabayashi et al., J. Neurosci. Res. 2010 88(5):1017-25. Antioxidants have been demonstrated to reduce free radicals and improve stem cell adhesion and stem cell survival during and following implantation. Song et al., Stem Cells 2010 28(3):555-63; Rodriguez-Porcel et al., Mol. Imaging Biol. 2010 12(3):325-34; Kashiwa et al., Tissue Eng. Part A. 2010 16(1):91-100. It is also known that resveratrol, a small molecule, enhances activity of endogenous antioxidants such as glutathione. superoxide dismutase (particularly manganese SOD), and catalase, and up-regulates the synthesis of stem cells themselves. Kao et al. Stem Cells Dev. 2010 19(2):247-58.

It has been demonstrated in animals that orally administered resveratrol helps to maintain a reduced cellular environment (less free radical activity) at a relatively low dose concentration (2.5 mg per kilogram of body weight, 175 mg per 160-lb human) which results in improved stem cell survival and enhanced cardiac function (ejection fraction, etc.). Gurusamy et al., J. Cell. and Mol. Medicine 14(9):2235-39 (2010). In particular, Gurusamy et al. reported that pre-treatment of rats with low dose resveratrol for two weeks prior to injection of cardiac stem cells into the myocardium significantly improved cardiac functional parameters such as left ventricular ejection fraction and fractional shortening. Pre-treatment also enhanced stem cell survival and proliferation as demonstrated by differentiation of stem cells towards the regeneration of the myocardium.

In accordance with a preferred embodiment of the present invention, a resveratrol composition of the present invention is administered orally to preserve stem cells following implantation. The results of administering this mixture include greater genomic response, and improved tissue function (i.e., heart muscle activity—ejection fraction) equal to or greater than what has been exhibited in prior experiments. The mixture of constituents is preferably provided in a capsule but may be in pill, tablet, or liquid form.

2. Macular Degeneration

The prolongation of the human lifespan over the past few decades in the US has spawned the proliferation of macular degeneration, an age-related eye disease. While not resulting in total vision loss, the disease robs older adults of their central vision used for reading as well as color vision. Macular degeneration affects the visual center of the eye, called the macula. The macula is part of the retina where color-vision cells (cones) are located.

In a preferred embodiment, the compositions of the present embodiments are co-administered to a subject with one or more macular degeneration or macular dystrophy treatments selected from the group consisting of an anti-angiogenic medicament (e.g., anecortave acetate, bevacizumab, bevasiranib, pegaptanib sodium, ranibizumab, etc.), an anti-drusen medicament (e.g., ARC1905, copaxone, eculizumab, fenretinide, RN6G, etc.) implantation of a miniature telescope into the eye, laser photocoagulation, photodynamic therapy, or administration of another therapy such as alprostadil, AREDS2, cortical implants, macular translocation, microelectrical stimulation, NT-501, photobiomodulation, radiation therapy, retinal implants or transplants, rheopheresis, cell transplantation (e.g., RPE cell transplantation, stem cell transplantation, etc.), submacular surgery, or a combination thereof.

The therapeutic benefits that may be shown in such macular-related embodiments include one or more benefits selected from the group consisting of preserved or improved eyesight (e.g., visual acuity), shrinkage or halting enlargement of visual defects, sparing cells in the central macula, permitting normal functioning of tissues surrounding or adjacent to the macula, decreases or prevention of increases in the amount of drusen or amyloid beta in the eyes, improving or increasing blood flow to the eye (and particularly the macula and retina), inhibition of blood vessel growth and leakage (e.g., angiogenesis), inhibition of scarring, improved retinal function, prevention or slowing of macular degeneration, prevention or slowing of cell death particularly retinal cells, reduction or elimination of eye lesions (e.g., geographic atrophy lesions), and combinations thereof.

In accordance with a preferred embodiment of the present invention, a resveratrol composition of the present invention is administered orally to: (1) limit oxidation in retinal tissues (photoreceptors, retinal pigment epithelial cells (RPE), choroid, specifically mitochondria and lysosomes in RPE cells); (2) inhibit accumulation of lipofuscin deposits; (3) inhibit formation of drusen; and (4) limit calcifications to retinal tissues, especially Bruch's membrane.

3. Cancer

A major challenge in cancer therapy is to selectively target cytotoxic agents to tumor cells (Luo, Y. et al. (2000) Biomacromolecules 1(2):208-218). To decrease undesirable side effects of small molecule anticancer agents, many targeting approaches have been examined. One of the most promising methods involves the combination or covalent attachment of the cytotoxin with a macromolecular carrier, and in particular with hyaluronic acid (Luo, Y. et al. (1999) Bioconjug. Chem. 10(5):755-763; Luo, Y. et al. (1999) Bioconjug. Chem. 12(6): 1085-1088; Luo, Y. et al. (2002) Pharm. Res. 19(4):396-402).

In one embodiment, the present embodiments relates to a resveratrol-composition of the present invention for the treatment of cancer. Upon provision with such composition, the sentinels of the innate immune system, dendritic cells, can be alerted and neutrophils, macrophages and natural killer cell activity can be significantly enhanced. This approach appears to be more appropriate for senior adults, the highest risk group for cancer, who are often immune-compromised due to poor nutrition or lack of nutrient absorption. The fact that this therapy can now be immediately measured for effectiveness by non-invasive cancer cell counting technology means that expensive and equivocal tests on animals may not be required to prove efficacy.

Resveratrol calms the response of phagocytes to foreign invaders like germs and tumor cells. Resveratrol dampens production of reactive oxygen species (free radicals) and normalizes particle ingestion in macrophage cells. Therefore, resveratrol prevents the over-response of immune cells that can produce autoimmunity.

Resveratrol blocks cancer in so many ways that it is difficult to find a pathway for cancer that is not obstructed by resveratrol. Resveratrol induces the cell energy compartments in tumor cells, called mitochondria, to release an enzyme called cytochrome C oxidase that usually leads to a cascade of other enzymes that induce programmed cell death, called apoptosis. But a recent experiment also shows that resveratrol releases cytochrome C from ovarian tumor cells that leads to rapid cell death via a process called autophagy, a process where enzymes produced inside the tumor cell actually digest its innards (kind of a form of intracellular cannibalism). This is a form of cell suicide that resveratrol activates in tumor cells, but not healthy cells.

The contribution of innate immunity in surveillance of tumors is comparatively neglected in cancer biology. Phagocytosis, or "cell eating" is the cornerstone of the innate immune response. Focus has been directed to dendritic cells which are believed to be sentinels of the innate immune response. A limited number of immune-boosting agents have been investigated. Skepticism surrounds interest in innate immune approaches to cancer treatment. For example, patients taking immune-suppressing agents don't necessarily develop cancer with more frequency. However, this may be misunderstood. An over-responsive immune system may lead to more tissue and organ damage that can be mortal to cancer patients. Most of the drugs used for breast cancer therapy induce immune suppression.

Nature's most potent iron chelator is inositol hexaphosphate (IP6), which is found in seeds and the bran fraction of whole grains. A low dosage of IP6 has been found to suppress the growth of rhabdomyosarcoma cells by 50%. Removal of IP6 allows these tumor cells to recover and grow once again. IP6-treated mice with injected tumors exhibit tumors that are 50 times smaller than non-treated mice. IP6 has also been shown to reduce the growth of injected fibrosarcoma cells in mice and prolong their survival. In examining the immune enhancing properties of IP6 it has been shown that it boosts production of free radicals (superoxide) and the cell digesting action of neutrophils in the presence of bacteria. IP6 increases the release of interleukin-8. The action of natural killer cells, which are involved in tumor cell destruction, is enhanced by IP6.

4. Aging

Calcification and rusting of cells impairs the cleansing of cellular debris (lipofuscin) from cells by enzymes produced by lysosomes, and results in impairment of cellular energy (ATP) produced by the mitochondria within cells. The compositions of the present embodiments inhibit and/or reverse cellular aging and/or connective tissue aging, and in particular, inhibit and/or reverse cellular aging and/or connective tissue aging caused by an accumulation of major minerals (e.g., iron, calcium, etc.). As a consequence, recipients of the compositions of the present embodiments exhibit enhanced longevity and enhanced cellular and connective tissue health and structure.

The human body ages at the cellular level by the slow accumulation of cellular debris called lipofuscin, which is facilitated by the progressive accumulation of iron and calcium within lysosomes and mitochondria. A cell cleansing and renewal process called autophagy prevents the accumulation of lipofuscin during the years of youthful growth, but this lysosomal mechanism declines once full growth is achieved due to accumulation of intracellular iron and calcium. Progressive inability to remove cellular debris results declining cell function and then premature death of the cell. A young cell efficiently removes debris from within. An old cell cannot efficiently remove debris and accumulates lipofuscin. The mitochondria, which provides cellular energy for lysosomal bodies to perform their cell cleansing activity, also becomes progressively calcified and ironized once childhood growth ceases. Only about 5% of mitochondria are functioning by age 80. Iron and calcium chelators are proposed to remedy mitochondrial aging which impacts cellular functions such as lysosomal enzymatic activity The human body ages within connective tissue by failure of cells called fibroblasts to regenerate collagen and hyaluronic acid, the latter being a space-filling, water-holding molecule. Collagen formation is facilitated by vitamins and amino acids in the diet (vitamin C, lysine, proline). Fibroblasts can be stimulated to produce hyaluronic acid by estrogen, made naturally in the body, and by estrogen-like molecules found in plants, called phytoestrogens, provided in the diet of by hyaluronic acid itself. Young females, by virtue of the ability to produce estrogen, exhibit thicker hair, smoother skin and more flexible joints, due to the abundance of hyaluronic acid. All of these being attributes of youthfulness.

In one embodiment, the present embodiments address both cellular and extracellular (connective tissue) aging, thus (a) preserving youthful function of living cells by removal of excess minerals, largely calcium and iron, from cells, this facilitating autophagy (cleanup of cellular debris, such as lipofuscin, via lysosomal enzymes) and (b) invigorating and preserving production of hyaluronan by stimulation of fibroblasts by HA, phytoestrogens (resveratrol, quercetin, genistein, are a few), to inhibition of degradation of HA by provision of metal chelators, such as phytic acid, ferulate, quercetin, resveratrol, etc.

In one embodiment, the dietary supplement addresses both cellular and extra-cellular aging by its ability to stimulate renewal of living cells from within via enzymatic degradation of cellular debris by intracellular lysosomal bodies. This is facilitated by the inclusion of metal (iron, copper, heavy metal) and calcium chelating molecules within the formula. Lysosomes lose their ability to enzymatically digest cellular debris with the progressive accumulation of iron, copper and other metals, and the crystallization of calcium. In another embodiment, the dietary supplement stimulates fibroblasts to produce hyaluronic acid at youthful levels again. This is accomplished by provision of orally-consumed molecules that stimulate fibroblasts to produce hyaluronic acid. In another embodiment, the dietary supplement includes metal chelating molecules that help maintain youthful lysosomal function are identified as antioxidants, like vitamin E or vitamin C, lipoic acid, metal chelators like IP6 phytate, quercetin, bioflavonoids or polyphenols, resveratrol. Resveratrol works by its ability to stimulate production of heme oxygenase, an enzyme that helps to control iron. The dietary supplement may also include molecules that inhibit crystallization of calcium are magnesium and IP6 phytate, and orally consumed molecules that stimulate fibroblasts to produce hyaluronic acid are hyaluronic acid, glucosamine, chondroitin, or estrogen-like molecules such as genistein, lignans, hydroxytyrosol, or other molecules configured like estrogen. Orally consumed HA stimulates greater HA and chondroitin synthesis. Similarly, glucosamine stimulate fibroblasts to produce HA. Alternatively, or additionally, glucosamine stimulates synovial production of hyaluronic acid, which is primarily responsible for the lubricating and shock-absorbing properties of synovial fluid" (McCarty, M. F. (1998) Medical Hypotheses 50:507-510, 1998). In yet another embodiment, the dietary supplement may include orally consumed molecules that stimulate production of collagen are vitamin C, proline and lysine.

The present embodiments relates to a method for restoring youthful function and appearance to human cells and tissues comprising the following steps: (a) stimulating renewal of living cells from within via enzymatic degradation of cellular debris by intracellular lysosomal bodies (preferably by providing a metal chelating molecule that helps maintain youthful lysosomal function, such molecules comprising antioxidants, such as vitamin E or vitamin C, lipoic acid, metal chelators like IP6 phytate, quercetin, bioflavonoids or polyphenols, and/or resveratrol); and (b) stimulating fibroblasts to produce hyaluronic acid (comprises providing orally consumed molecules that stimulate fibroblasts to produce hyaluronic acid, such orally consumed molecules comprising, for example, hyaluronic acid, glucosamine, chondroitin, and/or estrogen-like molecules such as genistein, lignans, hydroxytyrosol, or other molecules configured like estrogen). Preferably, such stimulation is achieved by the dietary administration of a composition comprising the stated compounds, more preferably in combination with an orally consumable molecule that stimulates production of collagen, such molecules comprising, for example, vitamin C, proline and/or lysine.

The individual components of the composition are believed to act synergistically to enhance the effect of, for example, resveratrol. Without intending to be limited thereby, it is proposed that the body's control or chelation of iron and calcium regulates the rate of aging after full growth has been achieved. During childhood growth all the iron and calcium are directed towards production of new bone and new red blood cells (hemoglobin). The cessation of childhood growth results in excess iron, copper and calcium, which then progressively (a) calcifies and (b) rusts tissues. The lysosomes begin to accumulate iron and calcium, which results in their dysfunction. The mitochondria begin to malfunction as they also progressively rust and calcify. The compositions of the present embodiments are believed to be capable of limiting or slowing the progressive rusting and calcification of cells and cellular organelles to thereby facilitate a slowing or reversal of the aging process. The chelation is what controls the genes. Genes are then favorably upregulated or downregulated. Resveratrol and a copper chelator are believed to act: (1) as controllers of calcium concentration via upregulation of osteocalcin, the hormone that helps retain calcium in bones and (2) as controllers of iron concentration via heme oxygenase, an antioxidant enzyme.

MAO inhibitors and iron chelators have been proposed as treatments for Parkinson's disease (Youdim, M. B. et al. (2004) J. Neural. Transm. 111(10-11):1455-1471; Yáñez, M. et al. (2006) Eur. J. Pharmacol. 542(1-3):54-60; Bureau, G. et al. (2008) J. Neurosci. Res. 86(2):403-410; Singh, A. et al. (2003) Pharmacol. 68(2):81-88; Gao, X. et al. (2007) Am. J. Clin. Nutr. 86(5):1486-1494; Johnson, S. (2001) Med. Hypotheses 56(2):171-173). The compositions of the present embodiments which contain the MAO inhibitor and copper chelator, resveratrol, the iron chelator and MAO inhibitor, quercetin, and the broad metal chelator, phytic acid are particularly preferred for the treatment of neurodegenerative diseases (especially Parkinson's Disease, camptocormia, and Alzheimer's Disease) or in the amelioration of the symptoms of such diseases.

C. Modulation of Gene Product Concentration or Activity

In an example embodiment, the compositions are capable of modulating gene expression to an extent greater than that observed with resveratrol alone or with calorie restriction. In a preferred embodiment, the specific activity of the resveratrol in a resveratrol-containing composition has been stabilized or enhanced. As used herein, the term "specific activity" refers to the ratio of the extent of gene modulation (relative to control) per amount (mass) of administered resveratrol. In another preferred embodiment, the compositions up-regulate a survival/longevity gene or down-regulate a gene whose expression enhances cellular damage upon administration to a recipient.

The embodiments pertains to compositions that, upon administration to a recipient, increase the concentration or activity of a survival/longevity gene product and/or decrease the concentration or activity of a gene product that induces or causes cellular damage. As used herein, such increase (or decrease) in concentration or activity may be accomplished by any mechanism. For example, such increase (or decrease) may reflect a modulation of gene expression resulting in either increased (or decreased) expression of the gene encoding the survival/longevity gene product, or a gene that regulates (e.g., induces or represses) or whose product regulates such expression or activity. Alternatively, or conjunctively, such increase (or decrease) in concentration or activity may reflect a modulation of the recipient's ability to degrade or stabilize any such gene products. Alternatively, or conjunctively, such increase (or decrease) in concentration or activity may reflect a modulation of the recipient's ability to enhance, accelerate, repress or decelerate the activity of any such gene products.

The modulation of concentration or activity discussed above may be a modulation of intracellular, intercellular and/or tissue concentration or activity of such survival/longevity gene products or such gene products that induce or cause cellular damage. Such modulation may be identified by assays of DNA expression, assays of gene product activity, assays of the level of gene product, assays of the rate of gene product turnover, etc. conducted in one or more types of cells, tissues, etc.

An increase in the concentration of a survival/longevity gene product may result from, for example, increased transcription of the gene that encodes the survival/longevity gene product, increased transcription of a gene that induces the expression of the gene that encodes the survival/longevity gene product, decreased transcription of a gene that represses the expression of the gene that encodes the survival/longevity gene product, decreased degradation or enhanced stabilization of expressed molecules of the survival/longevity gene product (leading to the enhanced accumulation of the survival/longevity gene product). Similarly, a decrease in the concentration of a survival/longevity gene product may result from, for example, decreased transcription of the gene that encodes the survival/longevity gene product, decreased transcription of a gene that induces the expression of the gene that encodes the survival/longevity gene product, increased transcription of a gene that represses the expression of the gene that encodes the survival/longevity gene product, increased degradation or decreased stabilization of expressed molecules of the survival/longevity gene product (leading to the enhanced dissipation of the survival/longevity gene product).

One aspect of the present embodiments thus relates to the use of resveratrol and resveratrol-containing compositions to modulate gene expression, and in particular, to modulate the expression of "survival/longevity" genes and/or "damage inducing" genes. As used herein, a compound is said to "modulate" gene expression if its administration results in a change in expression (relative to a control) of such genes of at least 10%. Modulation may involve an increase in expression ("up-regulation") or it may involve a decrease in expression ("down-regulation"). The term up-regulate thus denotes an increase of expression of at least 10%, at least 20%, at least 50%, at least 2-fold, at least 5-fold, or most preferably at least 10-fold (relative to a control). The term down-regulate conversely denotes a decrease of expression of at least 10%, at least 20%, at least 50%, at least 2-fold, at least 5-fold, or most preferably at least 10-fold (relative to a control).

A second aspect of the present embodiments relates to the use of resveratrol and resveratrol-containing compositions to modulate the concentration or activity of expressed products of "survival/longevity" genes and/or "damage inducing" genes. As used herein, a compound is said to "modulate" the concentration or activity of such expressed products if its administration results in a change in an intracellular, intercellular or tissue concentration or activity (relative to a control) of such gene products of at least 10%. Modulation may, for example, involve an "enhanced accumulation" or an "enhanced activity" or, for example, it may involve a "diminished accumulation" or a "diminished activity." The term "enhanced accumulation" (or "enhanced activity") denotes an increase in concentration (or activity) of at least 10%, at least 20%, at least 50%, at least 2-fold, at least 5-fold, or most preferably at least 10-fold (relative to a control). The term "diminished accumulation" or "diminished activity," conversely denotes a decrease in concentration (or activity) of at least 10%, at least 20%, at least 50%, at least 2-fold, at least 5-fold, or most preferably at least 10-fold (relative to a control).

As used herein, a "survival/longevity" gene is a gene whose expression contributes to an increase in the survival or longevity of a subject (e.g., a mammal, and particularly a human) expressing such gene. Conversely, a "damage inducing" gene is a gene whose expression contributes to DNA, cellular, or tissue damage in such subject. Such genes are responders to biological stressors, they initiate action in response to stressors such as radiation (e.g., sunlight, gamma rays, UV light, etc.), radiomimetic agents (e.g., vitamin D), heat, near starvation (calorie restriction, or its mimetic, resveratrol) by modulating their expression.

In a preferred embodiment, the survival/longevity gene is a sirtuin gene. The sirtuins are a conserved family of deacetylases and mono-ADP-ribosyltransferases, which have emerged as key regulators of cell survival and organismal longevity. Mammals have at least seven sirtuins, including Sirtuins 1 through 7. Sirtuin 1 is a nuclear deacetylase that regulates functions including glucose homeostasis, fat metabolism and cell survival. The Sirtuin 1 gene is known to control the rate of aging of living organisms by virtue of its ability to produce DNA repair enzymes and mimics the beneficial effects of calorie restriction. The trans form of resveratrol (but not cis-resveratrol) activates the Sirtuin 1 gene. The Sirtuin 3 gene is a mitochondrial sirtuin that regulates acetyl-CoA synthetase 2, and thus its modulation has physiological applications including increasing mitochondrial biogenesis or metabolism, increasing fatty acid oxidation, and decreasing reactive oxygen species. The role of Sirtuin 3 in promoting cell survival during genotoxic stress was demonstrated in U.S. Patent Application Publication No. 2011/0082189. Preferred embodiments particularly pertain to compositions that modulate (increase or decrease) the concentration of the Sirtuin 1 or Sirtuin 3 survival/longevity gene products, particularly as compared to the ability of resveratrol alone to modulate the gene products.

In particular, commercial formulations of Longevinex® have been shown to upregulate Sirtuin 3 at rates up to 2.95 times greater than resveratrol alone. Mukherjee et al., Can. J. Pharmol. Physiol. 2010 November; 88(11):1017-25. Sirtuin3 protein regulates manganese superoxide dismutase (Mn SOD) within the mitochondria, which may have direct affect upon aging, function and survival of the mitochondria with advancing age and in states of disease. Data also suggests that the commercial Longevinex® formulations lowered C-reactive protein (marker of inflammation), reduced insulin, raised HDL cholesterol and abolished impairment of flow-mediated arterial dilatation, the first sign of atherosclerotic disease.

Examples of survival/longevity genes and genes whose expression enhances cellular damage include, e.g., the genes disclosed in Tables 1 and 2, of U.S. patent application Ser. No. 12/212,494 filed on Sep. 17, 2008, which is herein incorporated by reference in its entirety. Most preferably, such genes are human genes. In a preferred embodiment, the compositions increase the concentration of the forkhead Foxo1 (daf-16, dFoxO) transcription factor survival/longevity gene product.

Some embodiments provide a composition that comprises trans-resveratrol and a metal chelating agent, and may additionally comprise quercetin, one or more glycosaminoglycans, and/or vitamin D. The trans-resveratrol may be encapsulated to substantially preserve the biological activity of the composition from loss due to exposure of the trans-resveratrol to light or oxygen. Particularly provided are compositions that comprise resveratrol, a chelator, hyaluronic acid, and/or vitamin D, and compositions which comprise the chelator phytic acid (inositol hexaphosphate; IP6), the glycosaminoglycan hyaluronic acid, and vitamin D.

Other embodiments provide resveratrol-containing compositions capable of modulating gene expression to an extent greater than that observed with resveratrol alone or with calorie restriction. The compositions may be used to up-regulate a survival/longevity gene or down-regulate a gene whose expression enhances cellular damage upon administration to a recipient, and may also be used in the treatment or prevention of cancer, cardiovascular disease, diseases associated with aging, and other conditions and illnesses. Particular embodiments provide a resveratrol-containing composition that, upon administration to a recipient, modulates the concentration or activity, relative to resveratrol alone or calorie restriction, of the product of a survival/longevity gene or the product of a gene whose expression enhances cellular damage. Administration is preferably by oral ingestion.

Particular embodiments provide compositions and methods where the modulation alters: (A) oxidative phosphorylation; (B) actin filament length or polymerization; (C) intracellular transport; (D) organelle biogenesis; (E) insulin signaling; (F) glycolysis; (G) gluconeogenesis; or (H) fatty acid metabolism. The gene product may be a survival/longevity gene product, and particularly Sirtuin 1, Sirtuin 3, or the forkhead Foxo1 transcription factor. The gene product may enhance cellular damage, and particularly may be encoded by the uncoupling protein 3, Pgc-1, or pyruvate dehydrogenase kinase 4 genes.

D. Packaging of the Compositions

Resveratrol is typically unstable to light and oxidation (Shaanxi University of Science & Technology, Xianyang China (2007) Zhong Yao Cai. 30(7):805-80). The resveratrol of the present embodiments is preferably prepared, packaged and/or stored in a manner that maximizes its specific activity. It is preferred to prepare, package and/or store resveratrol in low light (or in the dark) and/or in low oxygen, so as to minimize light-induced degradation (e.g., photo-isomerization) or oxygen-induced degradation. The preferred compositions of the present embodiments are formulated as dietary supplements for oral ingestion in the form of a pill, lozenge, capsule, elixir, syrup, etc. Other modalities of administration may alternatively be employed (e.g., intranasal, parenteral, intravenous, intraarterial, topical, etc.).

The resveratrol or plant extract comprising resveratrol is preferably encapsulated in a substantially oxygen-free environment. As used herein, the phrase "substantially oxygen-free" is intended to include environments having less than less than about 100 parts per million oxygen. Ideally, the encapsulation process would take place immediately after the extraction or formation of the small molecules and be shielded from exposure to light, heat, and oxygen. Alternatively, the material including small molecules may be stored in a substantially oxygen-free environment until encapsulated. The encapsulation process includes the steps of (1) providing a capsule including a head portion and a body portion; (2) at least partially filling the body portion with the material including biologically active small molecules; (3) axially positioning the head portion over the body portion such that the portions at least partially overlap; and (4) forming a fluid tight (air and liquid impermeable) seal along the overlapping portions.

The material comprising the capsule portions is not particularly limited. Preferably, the capsule portions comprise material possessing a low oxygen transmission rate. For example, it is preferred the capsule portions comprise a material having an oxygen transmission rate (as measured by ASTM D3985) of less than about 165 $cm^3/m^2$/day for 100 μm, more preferably less than about 4 $cm^3/m^2$/day for 100 μm, and most preferably less than about 1 $cm^3/m^2$/day for 100 μm. Exemplary materials comprising the capsule portions include, but are not limited to, an ingestible material such as gelatin, hydroxypropyl methylcellulose, or starch. By way of specific example, the material may include gelatin having an oxygen transmission rate of about 3.5 $cm^3/m^2$/day for 100 μm. The resulting capsules may include hard gelatin capsules or soft gelatin capsules having an oxygen transmission rate of up to about 0.04 $cm^3$/capsule/day (ASTM D3985 at 27° C. and rel. humidity of 50%). In addition, opaque capsules are highly preferred. This can be achieved by adding pigment such as titanium dioxide to the capsule material formulation. Titanium dioxide is inert and possesses a high molecular weight, which prevents it from being absorbed into blood circulation when ingested. Opaque capsules function to prevent the degradation of the resveratrol-containing composition by light degenerative processes such as photooxidation. A commercially available, opaque capsule having low oxygen permeability is available from Capsugel (Greenwood, S.C.—www.capsugel.com), sold under the trade name Licaps®.

The system used to encapsulate the composition including biologically active small molecules material must create a fluid-tight (air and liquid impermeable) seal around capsule portions. A particularly preferred encapsulation system and process is disclosed in WO 01/08631A1, incorporated herein by reference in its entirety. In this system and associated process, a capsule head portion and a capsule body portion are placed in a filling chamber. The capsule body portion is filled with the desired dosage material, and the capsule portions are then telescopically joined such that the head portion partially overlaps the body portion. A sealing liquid including a solvent is applied in the gap formed between the overlapping sections, and the capsule is dried to remove the solvent and form a fluid-tight seal.

It is important that the encapsulation process occurs in a substantially oxygen-free environment. In addition, it is preferred the encapsulation process take place in a darkened (substantially light free) environment. As explained above, small molecules such as resveratrol lose their biological activity upon exposure to light and/or oxygen (due, e.g., to oxidation processes). Consequently, the composition containing small molecules should be mixed and/or encapsulated in a system including airtight and darkened mixing and filling chambers having a substantially oxygen-free environment. This can be achieved by using an enclosed system from which oxygen is removed. Oxygen may be removed using a vacuum, replacing the oxygen within the system with an inert gas flush, or a combination thereof. For example, the system can be purged of oxygen using a controlled nitrogen blanket. In addition, the system is kept substantially oxygen free through the use of a nitrogen flush during the encapsulation process. A nitrogen purge may also be used to remove oxygen from each individual capsule. Specifically, prior to sealing, a positive pressure can be applied to each capsule to replace any oxygen present within the capsule with nitrogen. Upon sealing, a nitrogen bubble remains within the capsule. A commercially available encapsulation system capable of filling capsules in a substantially oxygen-free and light-free environment is available from Capsugel (Greenwood, S.C.—www.capsugel.com), sold under the trade name CPS 1000 Capsule Filling Machine.

In a preferred embodiment, the compositions of the present embodiments are formulated as air-tight capsules in which encapsulation is conducted so as to prevent or minimize exposure to oxygen. In one embodiment, such encapsulation is conducted in an oxygen-free environment. For example, the components of the compositions of the present embodiments may be inserted into a capsule in an inert gas (e.g., nitrogen, argon, etc.) environment. Preferably, a nitrogen bubble (e.g., 5-20% of the capsule volume) may be introduced into the capsule to further stabilize and protect the components against oxidation (see, PCT Publication No. WO 01/08631, herein incorporated by reference). That international application has a corresponding U.S. patent application. Suitable capsules useful in the encapsulation of resveratrol and other oxidation prone ingredients of dietary supplements include Licaps® (Capsugel), an air-tight gelatin capsule. The presence of phytic acid, which has the ability to protect the components from metal-induced oxidation, augments such anti-oxidation precautions. A particularly preferred example of such a resveratrol-containing composition is Longevinex® (Resveratrol Partners, LLC, San Dimas, Calif.), which comprises resveratrol and phytic acid. Longevinex® contains as active ingredients (per capsule): 5 mg Vitamin E (as mixed tocopherols), 215 mg total resveratrol (obtained from French red wine and giant knotwood (*Polygonum cuspidatum*), and providing 100 mg of trans-resveratrol), 25 mg quercetin dihydrate, 75 mg phytic acid (rice bran extract), 380 mg rice bran oil, 55 mg sunflower lecithin.

Once a composition has been sealed into an air-tight capsule, it is important to maintain a low or no-oxygen environment in the packaging surrounding the capsules in order to protect the composition from oxidation should a break or leak occur in the sealed capsule. Therefore, an oxygen absorbing packette is preferably employed to reduce the presence of free oxygen. Vacuum or nitrogen-flushed packaging (bottles, pill cases, etc.) in air-tight materials is desirable.

In an alternative embodiment, the components and compositions of the present embodiments may be prepared as a microencapsulated process (see, generally, Rubiana, M. et al. (2004) Current Drug Targets, 5(5):449-455). Micro-encapsulation is a process by which tiny particles or droplets (ranging in size from a few nanometers to one micron) are coated with a protective layer to create small capsules with controlled properties. Suitable micron-sized, encapsulated, preparations can be obtained using the microencapsulation processes of Maxx Performance Inc. (Chester, N.Y.), Blue California (Rancho Santa Margarita, Calif.), Southwest Research Institute (San Antonio, Tex.), Coating Place, Inc. (Verona, Wis.), Microtek Laboratories (Dayton, Ohio), Particle Sciences, Inc. (Bethlehem, Pa.), etc. $3^{rd}$-generation Longevinex® ("Longevinex-3®") (Resveratrol Partners, LLC), which contains Vitamin D3, Vitamin E, Resveratrol, Quercetin, and Phytic Acid is a particularly preferred microencapsulated form of the compositions of the present embodiments. The present embodiments further comprises a practical method of stabilizing quercetin and other easily oxidized dietary supplement ingredients which may come in contact with oxidizing metals.

Having now generally described the embodiments, the same will be more readily understood through reference to the following examples, which are provided by way of illustration and are not intended to be limiting of the present embodiments unless specified.

Example 1

Comparative Effects of Resveratrol and Compositions of the Present Embodiments

In order to determine if the compositions of the present embodiments are more effective than resveratrol alone in mediating a resveratrol biological activity, an analysis of gene expression is conducted, comparing the modulation of gene expression achieved by calorie restriction to the modulation of gene expression achieved by the compositions of the present embodiments.

Accordingly, the ability of resveratrol alone and the resveratrol-containing compositions of the present embodiments to up-regulate survival/longevity genes or down-regulate genes whose expression enhances cellular damage is compared using the expression profile of a calorie restricted ("CR") animal as a positive control and the expression profile of a normally fed animal as a negative control. Male B6CHF1 mice (2 months of age) are either placed on a 40% calorie restricted diet, provided commercially obtained trans-resveratrol (Sigma Chemical; 1.25 mg/kg per day), provided a resveratrol-containing composition of the present embodiments (Longevinex® plus nucleotides). The mice are monitored until they had reached five months of age, and body weight, serum glucose levels, serum insulin levels and lipid peroxidation in brain and muscle tissue are measured.

Example 2

Comparative Effects of Resveratrol and the Present Compositions on Gene Expression in Cardiac Tissue The profile of expressed genes in the cardiac tissue of mice receiving resveratrol or a composition of the present embodiments (Longevinex® with nucleotides) is compared to that of mice placed on a calorie restricted diet and control mice. Gene expression is monitored using an Affymetrix MG430 2.0 Array, containing 45,101 probe sets per array. In cases in which the array represented the same gene with multiple probes, the probe set with the highest signal intensity is employed. Unknown genes (including uncharacterized ESTs and cDNA sequences) are not analyzed. Analysis is conducted substantially as described by Lee, C.-K. et al. (2002) Proc. Natl. Acad. Sci. (U.S.A.) 99:14988-14993, herein incorporated by reference. It is expected that the present compositions will cause a statistically significant change in expression in treated vs. control mice or mice receiving resveratrol alone, particularly with regard to the up-regulation of survival/longevity genes and oxidative phosphorylation genes, which are involved in mitochondrial ATP production, and the down-regulation of genes whose expression enhances cellular damage, including the sirtuin family of genes, Pgc-1α, Uncoupling protein-3, and pyruvate dehydrogenase kinase 4.

The sirtuin family of genes, and in particular Sirtuin 1, are thought to be critical mediators of extended lifespans (Boily, G. et al. (2008) PLoS ONE 3(3):e1759; Huang, J. et al. (2008) PLoS ONE 3(3):e1710). Pgc-1α (peroxisome proliferative activated receptor, gamma, coactivator 1 alpha; ppargc1a) is a transcriptional co-factor that controls energy metabolism and mitochondrial biogenesis; its expression is increased in skeletal muscle tissue upon long-term calorie restriction (Conley, K. E. et al. (2007) Curr. Opin. Clin. Nutr. Metab. Care. 10(6): 688-692; Wu, Z. et al. (2007) Expert Opin. Ther. Targets 11(10):1329-1338). Uncoupling protein-3 is believed to be a target of Pgc-1α and to play a role in fatty acid metabolism; its expression is increased in cardiac tissue upon long-term calorie restriction (Bézaire, V. et al. (Epub 2007 Jan. 3) FASEB J. 21(2):312-324; Chan, C. B. et al. (2006) Curr. Diabetes Rev. 2(3):271-283). Pyruvate dehydrogenase kinase 4 coordinates fuel selection during fasting to promote fatty acid metabolism (Sugden, M. C. et al. (2006) Arch. Physiol. Biochem. 112(3): 139-149; Pilegaard, H. et al. (2004) Proc. Nutr. Soc. 63(2):

221-226; Sugden, M. C. (2003) Obes. Res. 11(2):167-169). It is a target of Pgc-1α and is induced in multiple tissues by long-term calorie restriction.

Example 3

Affected Biochemical Pathways

Recent research has suggested that complex traits are emergent properties of molecular networks that are modulated by complex genetic loci and environmental factors. Chen, Y. et al. (Epub 2008 Mar. 16) Nature 452(7186):429-435). Indeed, research within the last decade has revealed that most chronic illnesses such as cancer, cardiovascular and pulmonary diseases, neurological diseases, diabetes, and autoimmune diseases exhibit dysregulation of multiple cell signaling pathways (Harikumar, K. B. et al. (Epub Feb. 15, 2008) Cell Cycle. 2008:7(8)).

The compounds of the present embodiments are evaluated for their effect on the expression of biochemical pathways and are found to affect the expression of genes involved in multiple biological processes, such as the glucose metabolism pathway, the tricarboxylic acid metabolism pathway, the fatty acid metabolism pathway, and others.

Example 4

Model Mechanism of Action

The compounds of the present embodiments are determined to alter the expression of genes in key pathways of lipid metabolism, glucose metabolism, oxidative phosphorylation, the Kreb's cycle, ATP synthesis and fatty acid beta oxidation. Without intending to be bound by any mechanism of action, the compounds of the present embodiments are believed to act by enhancing the activity of the forkhead Foxo1 (daf-16, dFoxO) transcription factor. Studies in model organisms have shown that Foxo1 mediates lifespan expression by enhancing gene expression. Insulin/IGF-1 signaling phosphorylates Foxo1, thereby causing it to be excluded from the nucleus and downregulating its actions. The compounds of the present embodiments decrease insulin and IGF-1 signaling thereby decreasing Foxo1 phosphorylation. A proposed mechanism of action is that the compositions of the present embodiments deliver resveratrol to cells, where it passes through cell walls, enters the cytoplasm, and facilitates the translocation of Foxo1 gene into the cell nucleus, which produces longevity effects.

Example 5

Manufacture and Encapsulation of a Resveratrol Composition

Small molecules in the form of resveratrol were obtained via ethanol extraction from *Vitis vinifera* and *Polygonum cuspidatum*. The ethanol was removed, and the resulting extract comprised approximately 25% *vinis vinifera* skin resveratrol and 25% *polygonum cuspidatum* resveratrol, with the remainder comprising non-resveratrol, inert plant material. The biological activity of the resveratrol in the extract was confirmed using a SIRT1 Fluorescent Activity Assay/Drug Discovery Kit AK-555 (available from Biomol® Research Laboratories, Inc.; Plymouth Meeting, Pa.; www.biomol.com). The extract was kept in a nitrogen environment and added to a mixture including approximately 25% by weight quercetin; 33% by weight lecithin; and 9% phytic acid (in the form of rice bran extract). The remainder of the composition included approximately 33% by weight resveratrol extract.

The resulting slurry was placed into a capsule-filling machine. Individual dosages were encapsulated in gelatin capsules tinted with titanium oxide (Licaps® capsules available from Capsugel; Greenwood, S.C.; www.capsugel.com). The dosages were encapsulated in a substantially oxygen-free environment using a capsule-filling machine continually flushed with nitrogen (the Capsugel CFS 1000 Capsule Filling and Sealing Machine, available from Capsugel; Greenwood, S.C.; www.capsugel.com). Each resulting capsule included at least 15 mg resveratrol, 100 mg lecithin, 75 mg quercetin, and 25 mg phytic acid. These capsule samples were stored under ambient conditions for approximately eight months. The samples were tested for biological activity by determining whether each sample could activate sirtuin enzymes and, in particular, whether the samples stimulated SIRT1 catalytic activity. The samples were tested four months and eight months after encapsulation. Tests were performed using a SIRT1 Fluorescent Activity Assay/Drug Discovery Kit AK-555 (available from Biomol® Research Laboratories, Inc.; Plymouth Meeting, Pa.; www.biomol.com). Upon testing, it was determined that the resveratrol contained within the samples was biologically active, stimulating SIRT1 activity, producing up to about an eight-fold stimulation in enzymatic activity compared to when no resveratrol is present. Similarly, the biological activity of the quercetin was tested, and it was determined that the encapsulated quercetin maintained biological activity (i.e., the ability to stimulate SIRT1 activity compared to when no quercetin is present).

All publications and patents mentioned in this specification are herein incorporated by reference to the same extent as if each individual publication or patent application was specifically and individually indicated to be incorporated by reference in its entirety. While the embodiments has been described in connection with specific embodiments thereof, it will be understood that it is capable of further modifications and this application is intended to cover any variations, uses, or adaptations of the embodiments following, in general, the principles of the embodiments and including such departures from the present disclosure as come within known or customary practice within the art to which the embodiments pertains and as may be applied to the essential features hereinbefore set forth.

What is claimed is:

1. A method of treating macular degeneration in a human subject, comprising:
   administering to a human subject suffering from macular degeneration or macular dystrophy a composition comprising:
   trans-resveratrol in an amount of about 0.2 to about 2 mg per kg of body weight of the subject,
   a metal chelating agent in an amount of about 0.5 to about 3 mg per kg of body weight of the subject,
   one or more nucleotides in an amount of about 0.5 to about 2 mg per kg of body weight of the subject, and
   one or more additional phenolic antioxidants in a total amount of about 0.05 to about 2 mg per kg of body weight of the subject,
   wherein said administration is effective to improve the effectiveness of the macular degeneration treatment in the human subject as compared to administration of resveratrol alone.

2. The method of claim 1, wherein the administration is effective to provide one or more benefits selected from the group consisting of improved eyesight, shrinkage of visual defects, and decreased drusen in the eye.

3. The method of claim 1, further comprising co-administering to the human subject said composition, and a macular degeneration treatment selected from the group consisting of an anti-angiogenic medicament and an anti-drusen medicament.

4. A method of improving cell transplantation therapy in a human subject, comprising:
co-administering to a human subject transplanted cells and a composition comprising
trans-resveratrol in an amount of 0.25 to 5 mg per kilogram of the human subject,
a metal chelating agent, and
one or more additional antioxidants,
wherein said co-administration is effective to improve the effectiveness of the cell transplantation in the human subject as compared to administration of the transplanted cells alone.

5. The method of claim 4, wherein the co-administration is effective to improve survival of the transplanted cells.

6. The method of claim 4, wherein the co-administration is effective to improve proliferation of the transplanted cells.

7. The method of claim 4, wherein the transplanted cells are selected from the group consisting of cardiac stem cells, neural stem cells, and retinal pigment epithelial (RPE) cells.

8. The method of claim 4, wherein the transplanted cells are cardiac stem cells, and wherein the co-administration is effective to improve differentiation of the cardiac stem cells.

9. The method of claim 1, wherein the metal chelating agent comprises phytic acid.

10. The method of claim 1, wherein the one or more additional phenolic antioxidants are selected from the group consisting of apigenin, caffeic acid, epigallocatechin 3-gallate (EGCG), ferulic acid, and quercetin.

11. The method of claim 1, wherein the one or more additional phenolic antioxidants comprises tocotrienol.

12. The method of claim 11, wherein the tocotrienol is gamma-tocotrienol.

13. The method of claim 1, wherein the composition further comprises allicin in an amount of about 0.5 to about 2 mg per kg of body weight of the subject.

14. The method of claim 1, wherein the composition further comprises nucleotide precursors, nucleotide derivatives, ribonucleosides or deoxyribonucleosides.

15. The method of claim 4, wherein the metal chelating agent comprises phytic acid.

16. The method of claim 4, wherein the one or more additional phenolic antioxidants are selected from the group consisting of apigenin, caffeic acid, epigallocatechin 3-gallate (EGCG), ferulic acid, and quercetin.

17. The method of claim 4, wherein the one or more additional phenolic antioxidants comprises tocotrienol.

18. The method of claim 17, wherein the tocotrienol is gamma-tocotrienol.

19. The method of claim 4, wherein the composition further comprises allicin in an amount of about 0.5 to about 2 mg per kg of body weight of the subject.

20. The method of claim 4, wherein the composition further comprises nucleotide precursors, nucleotide derivatives, ribonucleosides or deoxyribonucleosides.

* * * * *